United States Patent [19]

Hejazi

[11] Patent Number: 5,376,806
[45] Date of Patent: Dec. 27, 1994

[54] STORAGE PHOSPHOR READER HAVING STORAGE PHOSPHOR SIZE AND EXPOSURE SPEED DETECTION

[75] Inventor: Shahram Hejazi, Webster, N.Y.

[73] Assignee: Eastman Kodak Company, Rochester, N.Y.

[21] Appl. No.: 85,862

[22] Filed: Jun. 30, 1993

[51] Int. Cl.5 .............................................. G03B 42/02
[52] U.S. Cl. .................................... 250/584; 250/587; 235/375
[58] Field of Search ................ 250/580, 584, 587, 585, 250/586; 235/375, 376, 462

[56] References Cited

U.S. PATENT DOCUMENTS

| | | | |
|---|---|---|---|
| 3,518,440 | 6/1970 | Hanson et al. | 250/219 |
| 3,566,083 | 2/1971 | McMillin | 235/61.11 |
| 3,760,162 | 9/1973 | Holter | 235/61.11 E |
| 3,819,938 | 6/1974 | Kornrumpf et al. | 250/222 R |
| 4,070,584 | 1/1978 | Chartraire et al. | 250/555 |
| 4,074,113 | 2/1978 | Gabriel | 235/419 |
| 4,088,265 | 5/1978 | Garczynski | 235/454 |
| 4,182,482 | 1/1980 | Muller et al. | 235/454 |
| 4,282,425 | 8/1981 | Chadima, Jr. et al. | 235/462 |
| 4,445,028 | 4/1984 | Huber | 235/472 |
| 4,498,006 | 2/1985 | Horikawa et al. | 250/327.2 |
| 4,500,776 | 2/1985 | Laser | 235/162 |
| 4,591,922 | 5/1986 | Takano et al. | 250/584 X |
| 4,638,170 | 1/1987 | Kubota | 250/566 |
| 4,641,242 | 2/1987 | Kimura | 364/414 |
| 4,734,566 | 3/1988 | Senda et al. | 235/455 |
| 4,739,480 | 4/1988 | Oono et al. | 250/584 X |
| 4,789,782 | 12/1988 | Ohara | 250/580 |
| 4,818,847 | 4/1989 | Hara et al. | 235/455 |
| 4,849,771 | 7/1989 | Lawrence et al. | 346/139 R |
| 4,885,468 | 12/1989 | Shimura | 250/327.2 |
| 4,960,993 | 10/1990 | Shigyo et al. | 250/327.2 |
| 5,021,642 | 6/1991 | Chadima, Jr. et al. | 235/472 |
| 5,038,024 | 8/1991 | Chadima, Jr. et al. | 235/472 |
| 5,051,567 | 9/1991 | Tedesco | 235/462 |
| 5,095,197 | 3/1992 | Chadima, Jr. et al. | 235/472 |
| 5,122,645 | 6/1992 | Saeki et al. | 235/462 |
| 5,128,519 | 7/1992 | Tokuda | 235/375 |
| 5,144,119 | 9/1992 | Chadima, Jr. et al. | 235/472 |
| 5,144,121 | 9/1992 | Chadima, Jr. et al. | 235/472 |
| 5,151,595 | 9/1992 | Filo | 250/317.1 X |
| 5,164,574 | 11/1992 | Ujiie et al. | 235/462 |
| 5,182,441 | 1/1993 | Chadima, Jr. et al. | 235/472 |
| 5,187,355 | 2/1993 | Chidima, Jr. et al. | 235/472 |
| 5,187,356 | 2/1993 | Chadima, Jr. et al. | 235/472 |
| 5,264,684 | 11/1993 | Weil | 250/580 X |

FOREIGN PATENT DOCUMENTS

1-238653 9/1989 Japan .................................... 250/584

*Primary Examiner*—Constantine Hannaher
*Assistant Examiner*—Edward J. Glick
*Attorney, Agent, or Firm*—William F. Noval

[57] ABSTRACT

Storage phosphor imaging system includes a source of stimulating light, a scanner for scanning a storage phosphor with a latent x-ray image with said stimulating light in a raster pattern to produce an emitted light x-ray image and a photodetector for converting the emitted light x-ray image into an x-ray image signal. The storage phosphor has associated with it a first bar code pattern of alternating bars and spaces for identifying the storage phosphor and a second bar code pattern of contiguous reflective/nonreflective cells for identifying storage phosphor exposure speed and storage phosphor size parameters. A first scanning bar code reader and a second bar code reader including a number of contiguous light emitter and photodetector assemblies, read the first and second bar code patterns, respectively, to produce signals used in identifying, reading and processing the storage phosphor and image signal.

4 Claims, 6 Drawing Sheets

STORAGE PHOSPHOR READER HAVING STORAGE PHOSPHOR SIZE AND EXPOSURE SPEED DETECTION

FIELD OF THE INVENTION

This invention relates generally to storage phosphor systems in which a latent x-ray image is recorded in a storage phosphor. A storage phosphor reader converts the stored latent x-ray image into an x-ray image signal. After conversion, the storage phosphor is erased and reused. This invention relates more particularly to a storage phosphor reader having storage phosphor size and exposure speed detection.

BACKGROUND OF THE INVENTION

In a storage phosphor imaging system as described in U.S. Pat. No. Re. 31,847, reissued Mar. 12, 1985, to Luckey, a storage phosphor is exposed to an x-ray image of an object, such as the body part of a patient, to record a latent x-ray image in the storage phosphor. The latent x-ray image is read out by stimulating the storage phosphor with relatively long wavelength stimulating radiation such as red or infrared light produced by a helium neon gas laser or diode laser. Upon stimulation, the storage phosphor releases emitted radiation of an intermediate wavelength, such as blue light, in proportion to the quantity of x-rays that were received. To produce a signal useful in electronic image processing the storage phosphor is scanned in a raster pattern by a laser beam deflected by an oscillating or rotating scanning mirror or hologon. The emitted radiation from the storage phosphor is reflected by a mirror light collector and detected by a photodetector, such as a photomultiplier, to produce an electronic image signal. Typically the storage phosphor is translated in a page scan direction past the laser beam which is repeatedly deflected in a line scan direction perpendicular to the page scan motion of the storage phosphor to form a scanning raster pattern of a matrix of pixels.

Typically, storage phosphors of different sizes and different x-ray exposure speeds are used in a diagnostic x-ray facility. Thus, different storage phosphor sizes are used in the x-ray exposure of different body parts, e.g., a larger size storage phosphor is needed for a chest x-ray than for a breast x-ray. Similarly, storage phosphors of different x-ray exposure speeds are used, for different diagnostic applications. Where different size storage phosphors are scanned, the scanning raster pattern size and scanning beam size may change. Such changes result in changing levels of emitted light which must be compensated either in reading the storage phosphor and/or in processing the read x-ray image signal. If the storage phosphor size and speed are encoded in a scanning type bar code associated with the storage phosphor, scanning such a bar code while the storage phosphor is moving can result in undesirable artifacts and reliability problems due to storage phosphor vibration. Such artifacts and reliability problems can result in improper reading and processing of an x-ray image signal. Moreover, bar code scanning devices are very expensive.

There is thus a problem in storage phosphor imaging systems of providing apparatus for detecting storage phosphor parameters such as size and exposure speed which is cost effective, reliable and artifact free.

SUMMARY OF THE INVENTION

According to the present invention, there is provided a solution to the problems of the prior art.

According to an aspect of the present invention, there is provided, a storage phosphor imaging system comprising: a storage phosphor which stores a latent x-ray image, and which has associated therewith a first bar code pattern of alternating bars and spaces for identifying the storage phosphor and a second bar code pattern of contiguous reflective/nonreflective cells for identifying both an exposure speed characteristic of the storage phosphor and a size characteristic of the storage phosphor; a first scanning bar code reader for reading the first bar code pattern associated with said storage phosphor and for producing a storage phosphor identification signal; a second bar code reader including a number of contiguous light emitter and photodetector assemblies for reading the second bar code pattern of contiguous reflective/nonreflective cells and for producing storage phosphor exposure speed and storage phosphor size signals; and a storage phosphor reader associated with said first and second bar code readers, for converting a latent image stored in said storage phosphor into an image signal; wherein said storage phosphor identification signal is linked to said image signal and wherein said storage phosphor exposure speed and size signals are used in reading said storage phosphor and/or processing said x-ray image signal.

DESCRIPTION OF THE PREFERRED EMBODIMENTS

Figure 1:
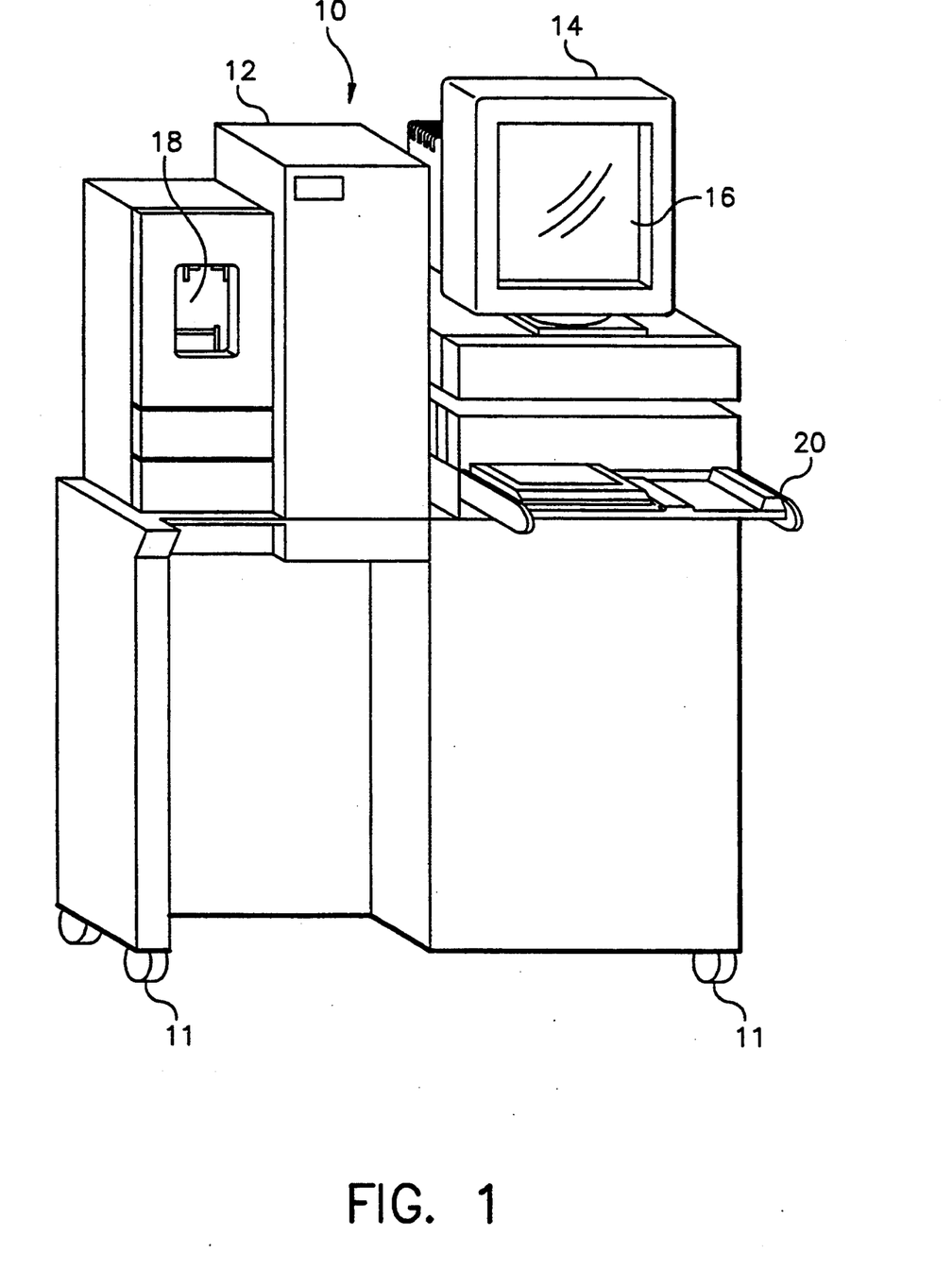
FIG. 1 is a perspective view of a storage phosphor reader incorporating the present invention.

Referring now to FIG. 1, there is shown a storage phosphor reader 10 incorporating an embodiment of the present invention. Reader 10 is mounted on casters 12 for easy portability in a radiology environment. Reader 10 includes a multiunit housing 12 housing the components of storage phosphor reader 10 and a video monitor 14 having a touch screen 16 supported on housing 12. Housing 12 also includes a bar code reader docking station 18 for docking a hand held bar code reader and for transferring data from the hand held bar code reader to storage phosphor reader 10. Reader 10 includes storage phosphor cassette load platform 20 which receives cassettes containing storage phosphor plates which are to be read or erased by reader 10.

In general, storage phosphor reader 10 processes images captured on a storage phosphor plate using conventional radiographic equipment. Reader 10 scans the storage phosphor plate and converts the latent x-ray image stored therein into an electrical x-ray image signal which can be viewed on monitor 14. The x-ray image signal is then delivered to a receiving device (such as a quality control station, laser printer or archival device) for image processing, image enhancement, viewing, printing and/or storage. The storage phosphor reader 10 is operated using touch screen 16 which also displays the image. The storage phosphor plates which are used to hold the unexposed x-ray images are mounted in standard size x-ray cassettes of different sizes. These storage phosphor plates are erased and reused repeatedly. The optional hand held bar code reader is used to collect exam information at the time the storage phosphor plate is exposed to an x-ray image. The exam information is transferred to the storage phosphor reader 10 when it is mounted in download station 18. The exam information is linked to a corresponding x-ray image signal read from the storage phosphor plate.

In general, the storage phosphor reader is usable in the storage phosphor patient identification system disclosed in commonly assigned U.S. patent application Ser. No. 963,036, filed Oct. 19, 1992, inventor Good et al. The storage phosphor patient identification system disclosed in the latter patent application is as follows:

When a radiology technologist receives a request for an x-ray examination of a patient, the technologist exposes a body part of the patient to an x-ray which is stored as a latent x-ray image in the storage phosphor plate of a storage phosphor cassette. Several images may be taken at this time. Using the optional portable bar code reader the technologist scans the patient identification bar code label and the label on the storage phosphor cassette. Exam related information can be scanned from a bar code chart that is usually attached to the portable x-ray generator. Such information includes body part type, x-ray exposure conditions, position of patient and the like.

The image is now captured by the technologist performing the x-ray exam using the cassette containing the storage phosphor plate from which the bar code label was scanned. When the x-ray exam is complete the technologist takes the storage phosphor cassette to storage phosphor reader 10 to be processed. If the optional bar code reader is used, the technologist transfers the patient identification and exam information by inserting the bar code reader into the bar code reader station 18 on the front of reader 10. The scanned information is then transferred to the control system of the storage phosphor reader 10. The technologist then loads the cassette containing the exposed storage phosphor plate into reader 10 by loading it on load platform 20. Scanning is initiated when the technologist presses a start button on touch screen 16.

Inside storage phosphor reader 10 the storage phosphor plate is extracted from the cassette and scanned with a laser light to produce an x-ray image signal. As the plate is scanned, the image appears on touch screen 16 as it is being scanned. After the scanning is complete, the x-ray image signal is sent to a receiving device where it can be tonescaled, enhanced, viewed, printed and/or stored. After the storage phosphor plate has been completely scanned it is erased by exposure to light which removes any residual image stored in the storage phosphor. The storage phosphor reader 10 then places the storage phosphor plate back into its cassette. The technologist can now remove the cassette from reader 10 to be reused for another exam.

Figure 2:
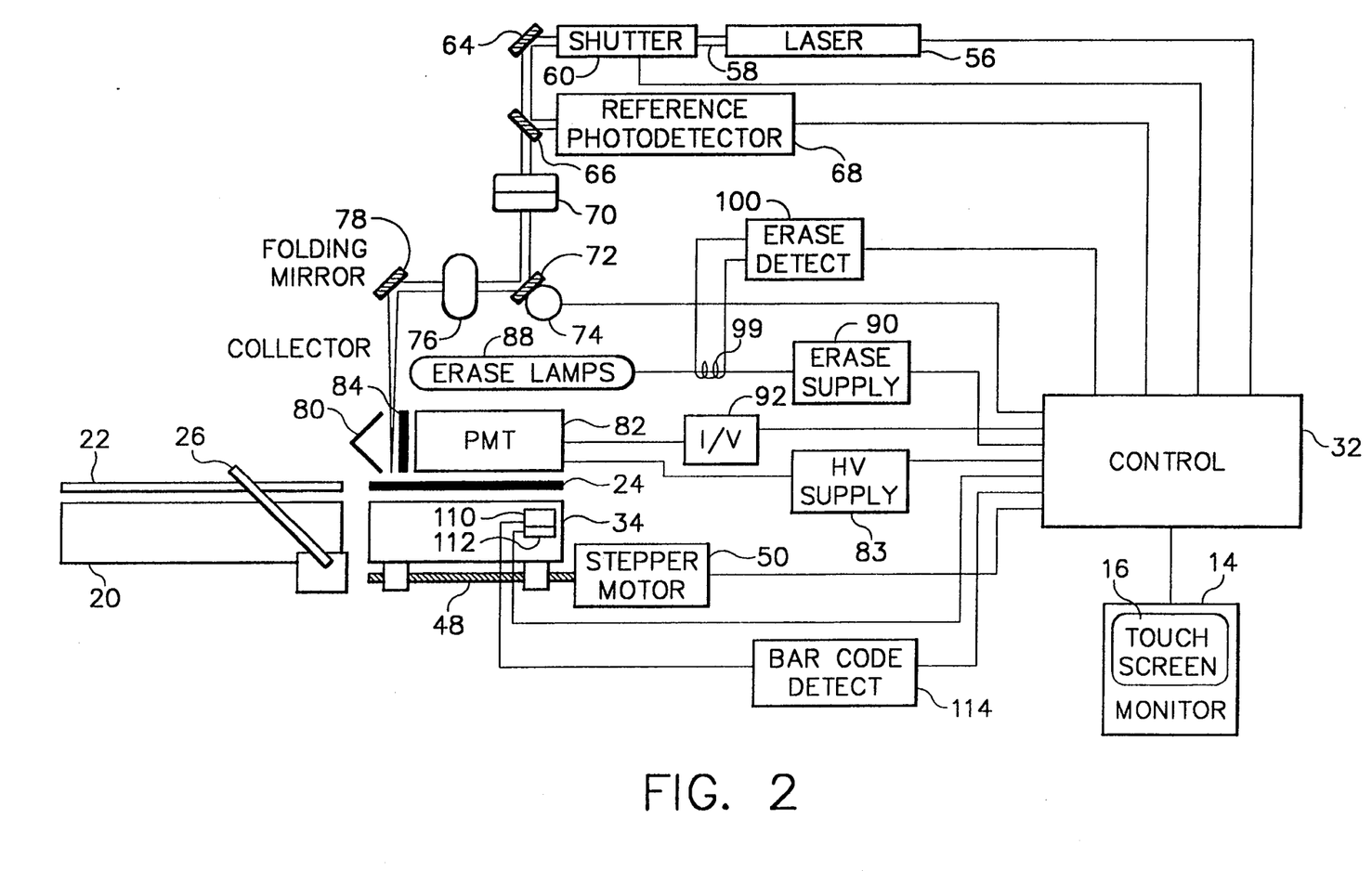
FIGS. 2 and 3 are respectively a partially diagrammatic, partially schematic view and a perspective view of components of the storage phosphor reader of FIG. 1.
Figure 3:
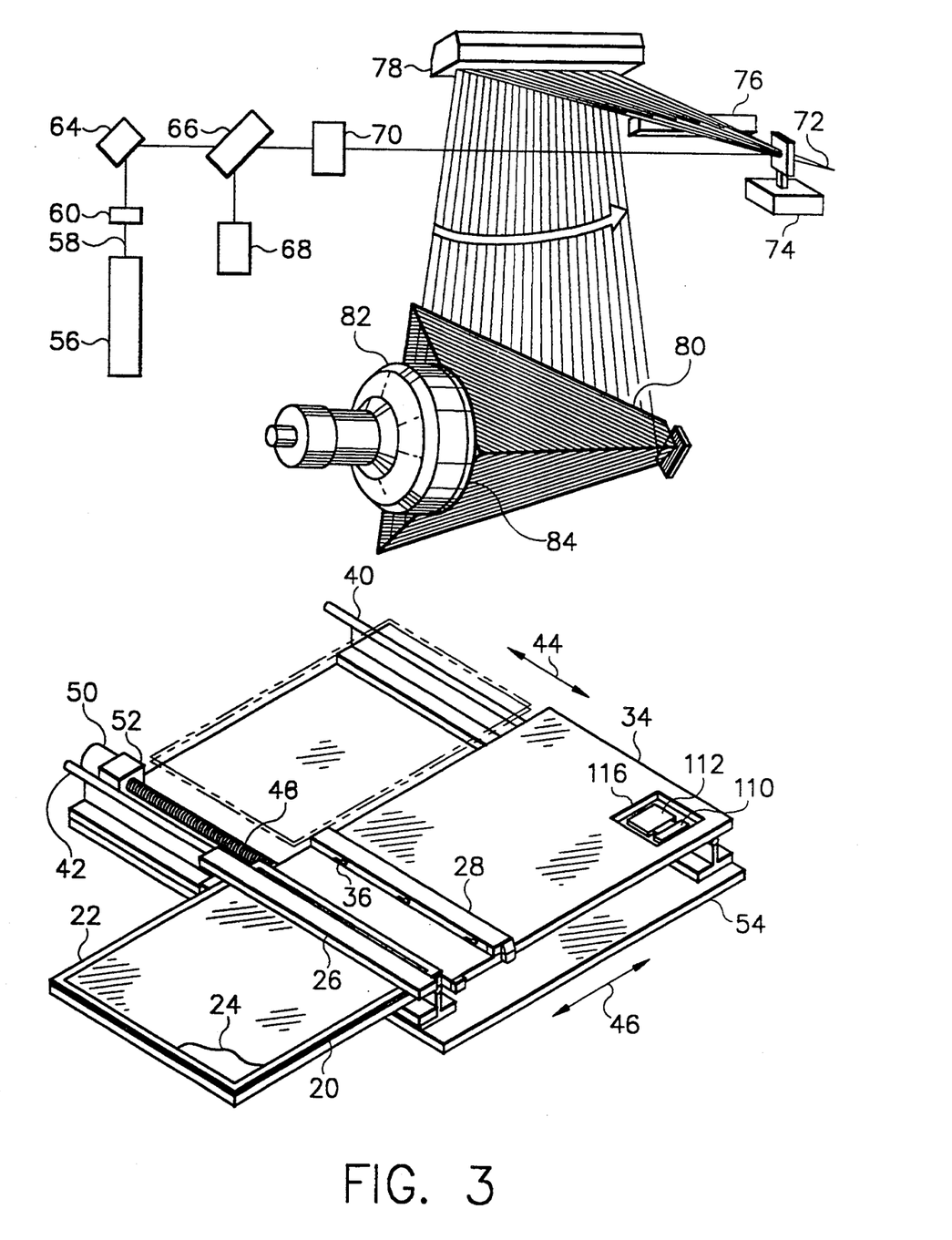

Referring now to FIGS. 2 and 3 there will be described in greater detail a preferred embodiment of storage phosphor reader 10 incorporating the present invention. As shown, a storage phosphor cassette 22 containing a storage phosphor plate 24 is loaded on cassette load platform 20. Load lever 26 is rotated to clamp cassette 22 in place and to unlatch the cassette 22 to permit extraction of storage phosphor plate 24 therefrom. Storage phosphor plate 24 is extracted from cassette 22 by extraction device 28 (FIG. 3) which is under software control from control 32. Control 32 includes standard computer components such as a microprocessor, a magnetic disk drive for storing images, software applications and a computer operating system, and input and output devices to communicate with the components of reader 10. Such microcomputer systems are well known in the art and will not be described in detail herein.

Extraction device 28 is slidably mounted on translation stage 34 and includes hooks 36 which engage storage phosphor plate 24. Extraction device 28 extracts storage phosphor plate 24 from cassette 22 onto translation stage 34.

Translation stage 34 is slidably mounted on rails 40 and 42 for movement in opposite directions 44 which are perpendicular to the directions 46 of loading and unloading of plate 24 relative to translation stage 34. Translation stage 34 is driven by a screw drive mechanism 48 actuated by stepper motor 50 mounted on block 52. Rails 40 and 42 are supported by frame member 54 of reader 10.

The laser scanning components will now be described. Reader 10 includes a laser 56 (such as a helium neon gas laser or a diode laser) for stimulation of storage phosphor plate 24. Laser 56 produces a laser beam 58 which passes through a shutter 60. Shutter 60 is controlled by digital signals received from control 32. Shutter 60 closes with activation of cover interlock switches 62 which detect closure of the housing 12 covers.

Beam 58 is reflected off mirror 64 and passes through beam splitter 66 which directs a portion of the laser beam 58 to reference photodetector 68. Following the beam splitter 66 laser beam 58 passes through collimator 70. The collimated laser beam is deflected by an oscillating scan mirror 72 driven by galvanometer 74 under the control of control 32. Scan mirror 72 provides the line scan raster motion of the laser beam 58. Galvanometer 74 drives mirror 72 with a constant angular velocity.

An f-theta lens 76 produces a flat field of focus and constant linear velocity at the plane of storage phosphor plate 24 for laser beam 58. Folding mirror 78 directs the laser beam through light collector 80 onto storage phosphor plate 24. Collector 80 may be of the type disclosed in commonly assigned U.S. Pat. No. 5,151,592, issued Sep. 29, 1992, inventors Boutet et al. The stimulating light of laser beam 58 causes the storage phosphor in plate 24 to emit light (blue) which is a function of the x-ray image stored in plate 24. Collector 80 directs this emitted light onto a photodetector, such as, photomultiplier tube (PMT) 82 which converts the emitted light into an x-ray image signal. PMT 82 is powered by high voltage supply 83. A filter 84 in front of the face of PMT 82 blocks the scattered stimulating laser light and passes the light emitted by storage phosphor plate 24.

Once a storage phosphor plate 24 is completely moved on to translation stage 34, a scan is begun. Movement of translation stage 34 in the direction of arrow 44 is under software control of control 32. Control 32 sends commands to stepper motor 50 to initiate a scan, to start translation stage 34, to start galvanometer 74 and to turn on PMT 82. From the home position of stage 34 the control 32 controls stepper motor 50 to move the stage 34 to the point where the storage phosphor plate 24 is under collector 80. At this point, conversion of the latent x-ray image stored in storage phosphor plate 24 into an x-ray image signal begins. At the end of the scan (determined by the number of scan lines for the appropriate storage phosphor plate size), PMT 82 and galvanometer 74 are turned off and translation stage 34 is returned to the home position.

Immediately after translation stage 34 reaches the home position, an erase lamp assembly 88 is turned on by actuation of erase power supply 90 under software control from control 32. Following a predetermined erase time (such as 30 seconds) erase lamp assembly 88 is turned off and extraction mechanism 28 returns storage phosphor plate 24 in the direction of arrow 46 to storage phosphor cassette 22. During the erase time, stage 34 and extraction mechanism 28 are disabled to prevent removal of plate 24 until erasure is complete. The storage phosphor reader user can now remove cassette 22 from loading platform 20.

During the scan of storage phosphor plate 24 an emitted x-ray light image is converted by PMT 82 into an x-ray image signal. This signal is converted to a voltage by I/V amplifier 92. Laser noise which is present in the x-ray image signal produced by PMT 82 is corrected by subtracting a reference signal detected by reference photodetector 68. The corrected digital signal is corrected for the light collection signature of light collector 80 by a correction lookup table in control 32. The correction lookup table is loaded during calibration of reader 10 when it is initially set up.

Erase lamps 88 are monitored by an electromagnetic field current sensor 99 and erase failure detect circuit 100 (FIG. 2) to detect a failure of one or more lamps.

Patient identification, examination information, and storage phosphor identification number are downloaded into reader 10 from a hand held bar code scanner positioned in station 18 of reader 10. According to the present invention, storage phosphor plate 24 has associated with it; (1) a first bar code pattern 120 of alternating bars and spaces for identifying the storage phosphor 24; and (2) a second bar code pattern 122 of contiguous reflective/nonreflective cells for identifying parameters of the storage phosphor, including storage phosphor size and storage phosphor exposure speed. As shown in FIGS. 2 and 3, reader 10 is provided with a first scanning bar code reader 110 for reading the first bar code pattern 120 associated with said storage phosphor 24, and for producing a storage phosphor identification signal, which is transmitted to control 32.

Reader 10 is also provided with a second bar code reader 112 for reading the second bar code pattern 122 of contiguous reflective/nonreflective cells, and for producing storage phosphor parameter signals, such as storage phosphor size and storage phosphor exposure speed signals. The latter signals are transmitted to detection circuit 114 which processes them before transmission to control 132.

As described above, the storage phosphor identification signal produced by first bar code reader 110 links the x-ray image signal read from storage phosphor 24 with the examination information and patient identification information which was downloaded from the hand held bar code reader at station 18 (FIG. 1).

Figure 4:
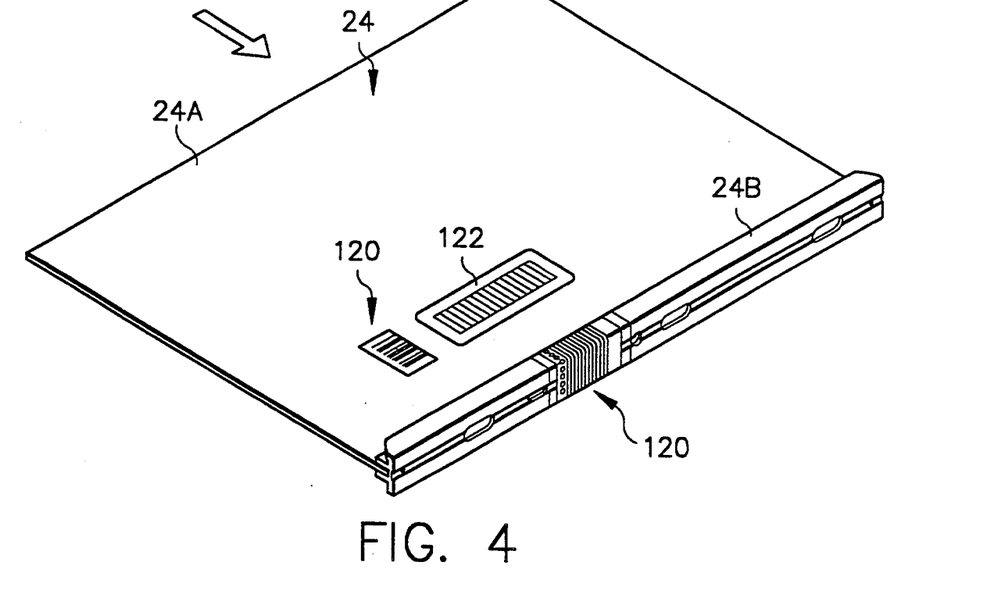
FIG. 4 is a schematic diagram of a storage phosphor image plate showing first and second bar code patterns.

As shown in FIG. 4, first and second bar code patterns 120 and 122 are located next to one another on the lower side 24a of storage phosphor 24. First bar code pattern 120 is also located on the front member 24b of storage phosphor 24 so that it can be read when storage phosphor 24 is located in cassette 22 (for example, at the time storage phosphor 24 is exposed to an x-ray image).

Figure 5A:
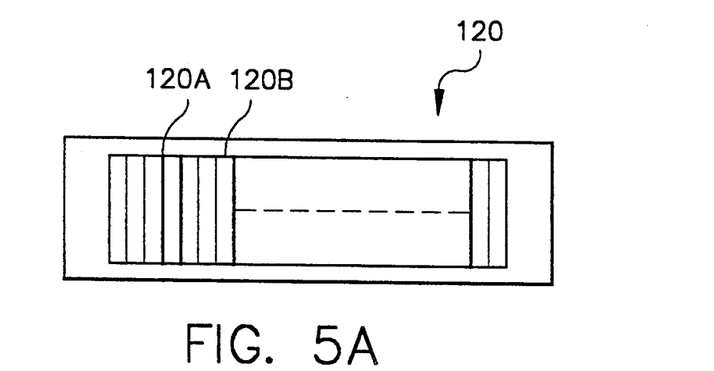
FIG. 5a is a diagrammatic view of an embodiment of alternating bars and spaces bar code pattern.

FIG. 5a shows first bar code pattern 120 as including alternating bars 120a and spaces 120b. Bar code pattern 120 may take the form of one of many standard scanning bar code patterns (e.g., EAN/UPC-A and E, CODE39, CODABAR, Interleave 2 of 5, CODE128).

Figure 5B:
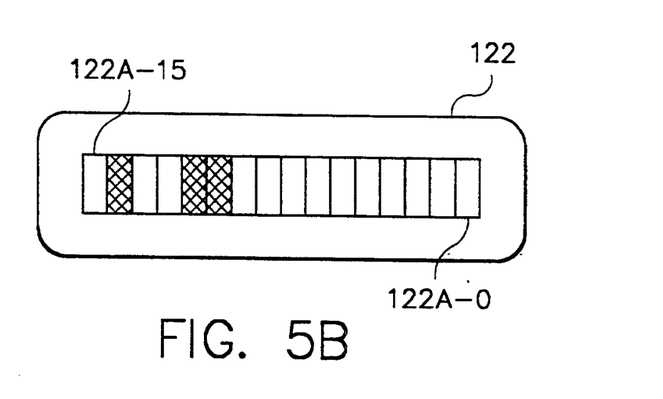
FIG. 5b is a diagrammatic view of an embodiment of reflective/nonreflective bar code pattern.

FIG. 5b shows second bar code pattern 122 as including contiguous cells 122a which are reflective (light) and nonreflective (dark). Bar code pattern 122 is shown as including sixteen cells 122a-0 to 122a-15 representing binary bits 0-15. If the cell is reflective (light), it represents a binary "1", and if the cell is nonreflective (dark), it represents a binary "0".

As an example, cells 122a-0–122a-8 (bits 0-8) are encoded for the exposure speed of storage phosphor 24. (For example, a value of 0 through 511 may be encoded). Cells 122a-9–122a-11 can be encoded for various cassette sizes; i.e., eight different storage phosphor (cassette) sizes. An exemplary encoding is as follows:

TABLE 1

| Cassette Size | Bit 11 | Bit 10 | Bit 9 |
| --- | --- | --- | --- |
| Test | 0 | 0 | 0 |
| 35 × 43 cm | 0 | 0 | 1 |
| 35 × 35 cm | 0 | 1 | 0 |
| 24 × 30 cm | 0 | 1 | 1 |
| 18 × 24 cm | 1 | 0 | 0 |
| 30 × 35 cm | 1 | 0 | 1 |

Cells 122a-12–122a-14 (bits 12-14) are unused in this example, and cell 122a-15 (bit 15) is an even parity bit for all bits 0-14.

As shown in FIG. 3, first and second bar code readers 110 and 112, are located below an aperture 116 in stage 34 of reader 10. After extraction mechanism 28 has extracted a storage phosphor 24 from cassette 22 and full positioned it on translation stage 34, bar code readers 110 and 112 read bar code patterns 120 and 122 while storage phosphor 24 is stationary.

Figure 6:
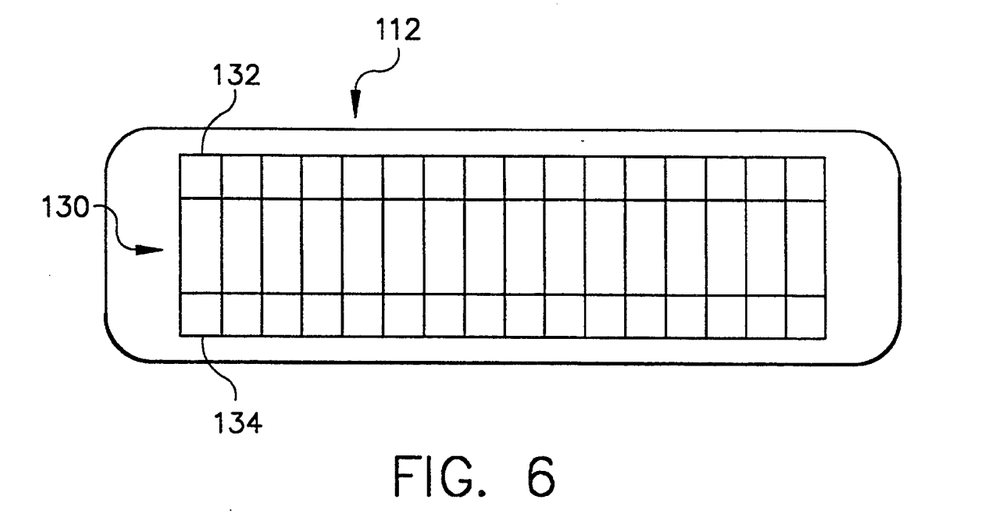
FIGS. 6 and 7 are top plan and side elevational views of an embodiment of a second bar code reader used in the reader of FIG. 1.
Figure 7:
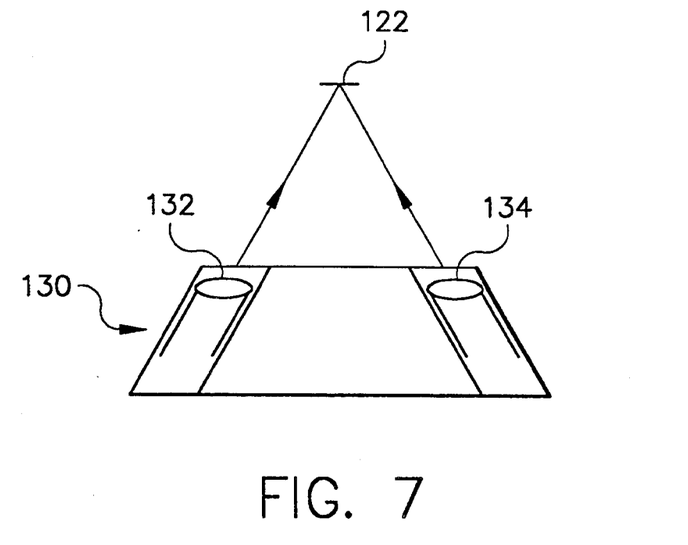

As shown in FIGS. 6 and 7, second bar code reader 112 includes a plurality of contiguous reflective sensors 130. Each sensor 130 includes an infrared photodiode 132 and a phototransistor 134 placed at an angle which corresponds to the focal length of the sensor. In the bar code reader 112 shown, sixteen sensors are placed in a one dimensional array. There are an equal number of sensors 132 as there are cells 122a in bar code pattern 122. Sensors 130 produce signals which are conditioned by individual circuits in detection circuit 114.

Figure 8:
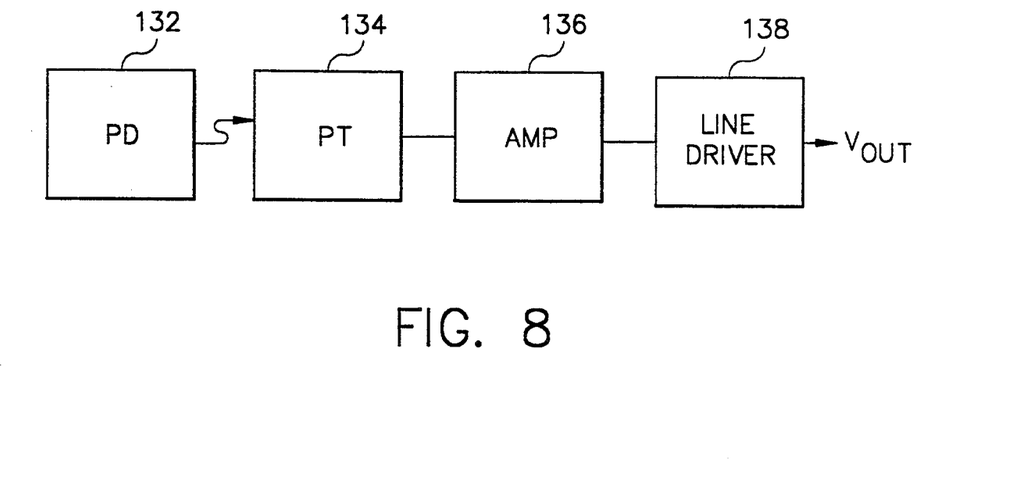
FIGS. 8 and 9 are, respectively, a schematic diagram and a block diagram of bar code detection circuits.

As shown in block diagram in FIG. 8, each detection circuit includes photodiode (PD) 132 which emits a light beam which is either reflected from or absorbed by a cell 122. Phototransistor (PT) 134 produces a signal which is amplified by amplifier 136 and followed by a line driver 138 with hysteresis that improves the signal-to-noise ratio.

Figure 9:
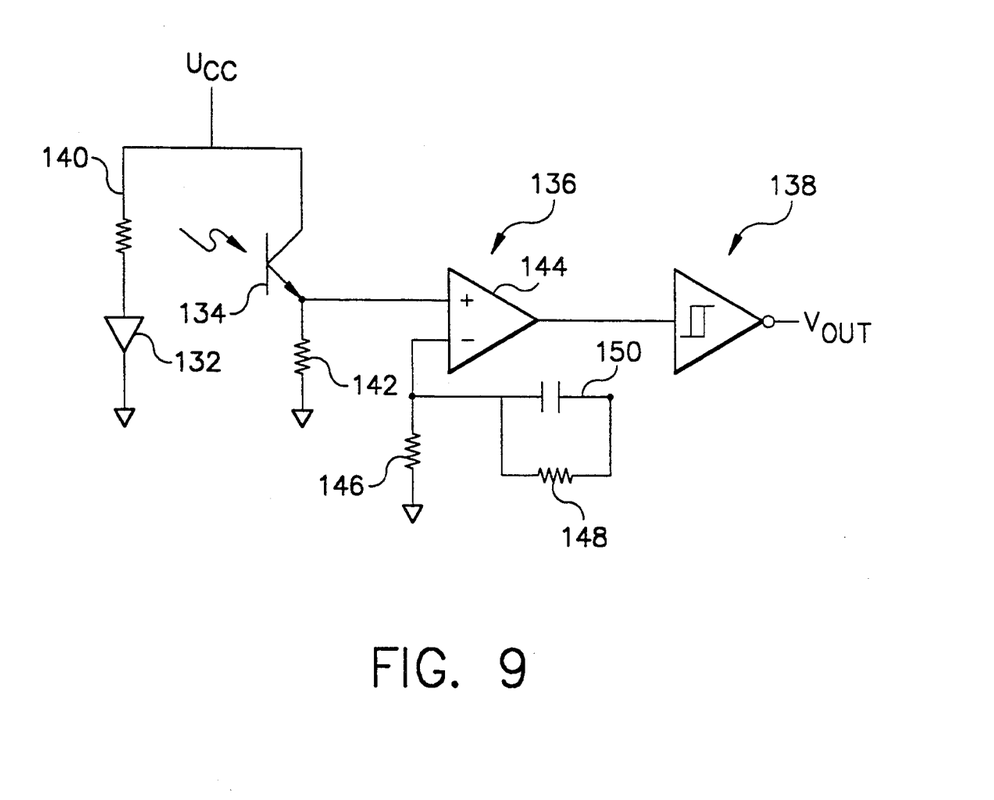

FIG. 9 is a schematic diagram of the circuit shown in FIG. 8. Photodiode 132 and phototransistor 134 are respectively connected, (1) to a voltage Vcc, by resistor 140 and directly, and (2) to ground, directly and by resistor 142. Photodiode 132 and phototransistor 134 may, for example, be an Optek OPB742 reflective sensor. Amplifier 136 includes an opamp 144, the "+" input of which is connected to the emitter of phototransistor 134. The "−" input of opamp 144 is connected to ground by resistor 146 and to the output of opamp 144 by the parallel combination of resistor 148 and capacitor 150. Amplifier 144 may, for example, be an LT1079 opamp. Opamp 144 is preferably an FET type which has very low bias current, thus making it suitable for amplification of phototransistor signals. This amplifier runs on a single voltage source, which eliminates the need for a dual voltage supply. The exemplary LT1079 is also available in a space saving quad (4) package. Line driver 138 may, for example, be a 74LS240.

The gain of amplifier 136 may be adjusted according to the reflectivity of the bar code cell used to produce a positive output for a reflective surface and a negative (zero) output for a nonreflective (black) surface. The optimum focal length of the detector is 0.15 inches and hence the sensors 130 are mounted so that their distance from the bar code pattern 112 is about 0.15 inches. This distance is important since the output gain decreases rapidly as this distance varies, e.g., the gain drops to 50% as this distance decreases to 0.06 inches, or increases to 0.22 inches.

Bar code reader 112 is not a scanning type system, as is bar code reader 110. Each sensor 130 will read the bar code cell that is positioned in front of it only when the cell is at rest. Such a bar code reader is more reliable, easier to implement, and considerably less expensive than a scanning system.

The present invention finds application in medical diagnostic imaging systems, such as storage phosphor imaging systems.

Although the invention has been described with reference to preferred embodiments thereof, it will be understood that variations and modifications can be effected within the spirit and scope of the invention as described above and as defined in the appended claims.

What is claimed is:

1. A storage phosphor imaging system comprising:
   a storage phosphor which stores a latent x-ray image, and which has associated therewith a first bar code pattern of alternating bars and spaces for identifying the storage phosphor and a second bar code pattern of contiguous reflective or nonreflective cells for identifying both an exposure speed characteristic of the storage phosphor and a size characteristic of the storage phosphor;
   a first scanning bar code reader for reading the first bar code pattern associated with said storage phosphor and for producing a storage phosphor identification signal ;
   a second bar code reader including a number of contiguous light emitter and photodetector assemblies for reading the second bar code pattern of contiguous reflective or nonreflective cells and for producing storage phosphor exposure speed and storage phosphor size signals; and
   a storage phosphor reader associated with said first and second bar code readers, for converting a latent x-ray image stored in said storage phosphor into an x-ray image signal; wherein said storage phosphor identification signal is linked to said image signal and wherein said storage phosphor exposure speed and size signals are used in reading said storage phosphor and/or processing said x-ray image signal.

2. The storage phosphor imaging system of claim 1 wherein said first and second bar code patterns are located on said storage phosphor and said first and second bar code readers are positioned to read said first and second bar code patterns on said storage phosphor before said storage phosphor reader converts said latent x-ray image into said x-ray image signal.

3. The storage phosphor imaging system of claim 1 wherein said light emitter and photodetector assemblies emit and detect infrared light.

4. The storage phosphor imaging system of claim 1 wherein said storage phosphor reader includes a translation assembly for translating a storage phosphor as it is read by said storage phosphor reader and wherein said second bar code reader is positioned relative to said translation assembly to read said bar code when said storage phosphor is stationary.

* * * * *